United States Patent
Bharadwaj et al.

(10) Patent No.: US 9,420,148 B2
(45) Date of Patent: Aug. 16, 2016

(54) HIGH-THROUGHPUT SINGLE-CELL IMAGING, SORTING, AND ISOLATION

(71) Applicants: Rajiv Bharadwaj, Emeryville, CA (US); Bahram Fathollahi, Palo Alto, CA (US)

(72) Inventors: Rajiv Bharadwaj, Emeryville, CA (US); Bahram Fathollahi, Palo Alto, CA (US)

(73) Assignee: CALIPER LIFE SCIENCES, INC., Hopkinton, MA (US)

( * ) Notice: Subject to any disclaimer, the term of this patent is extended or adjusted under 35 U.S.C. 154(b) by 0 days.

(21) Appl. No.: 14/886,351

(22) Filed: Oct. 19, 2015

(65) Prior Publication Data

US 2016/0044212 A1 Feb. 11, 2016

Related U.S. Application Data

(63) Continuation of application No. 14/595,693, filed on Jan. 13, 2015, now Pat. No. 9,165,359, which is a continuation of application No. 13/783,767, filed on Mar. 4, 2013, now Pat. No. 8,934,700.

(51) Int. Cl.

| | |
|---|---|
| *G06K 9/00* | (2006.01) |
| *H04N 5/225* | (2006.01) |
| *G06T 7/00* | (2006.01) |
| *B01L 3/00* | (2006.01) |
| *C12M 1/00* | (2006.01) |
| *C12N 5/00* | (2006.01) |
| *H04N 7/18* | (2006.01) |
| *G02B 21/36* | (2006.01) |
| *C12N 13/00* | (2006.01) |

(52) U.S. Cl.
CPC ......... *H04N 5/2251* (2013.01); *B01L 3/502761* (2013.01); *C12M 47/04* (2013.01); *C12N 5/0081* (2013.01); *C12N 5/0087* (2013.01); *G02B 21/365* (2013.01); *G06T 7/0012* (2013.01); *H04N 5/2256* (2013.01); *H04N 7/18* (2013.01); *B01L 2200/0636* (2013.01); *B01L 2200/0652* (2013.01); *B01L 2200/0668* (2013.01); *B01L 2300/0816* (2013.01); *B01L 2300/0864* (2013.01)

(58) Field of Classification Search
USPC ......... 382/100, 103, 107, 128–134, 162, 168, 382/173, 181, 209, 219, 224, 232, 254, 274, 382/276, 291, 305, 312; 435/288.7, 173.9, 435/6.13, 6.11; 422/50; 209/579
See application file for complete search history.

(56) References Cited

U.S. PATENT DOCUMENTS 8,021,614 B2 * 9/2011 Huang .............. B01L 3/502746
422/50

(Continued)

*Primary Examiner* — Seyed Azarian
(74) *Attorney, Agent, or Firm* — Cardinal Law Group

(57) ABSTRACT

The invention provides a method and apparatus for isolating individual target cells. The apparatus includes a body structure comprising a main channel, a collection channel, and a waste channel fluidly coupled at a first fluid junction. A plurality of trapping channels intersect the collection channel, each trapping channel having a diameter at a location adjacent to the intersection of the trapping channel with the collection channel that is less than a diameter of an individual target cell. The apparatus also includes an imaging system configured to image individual target and non-target cells within the main channel, thereby producing imaging data; a processor configured to perform real-time, multivariate analyses of the imaging data; and a directing system configured to direct the individual target cells. A pressure source is in fluid communication with one or more of the collection channel, the waste channel, the first side channel, and the second side channel.

23 Claims, 3 Drawing Sheets

(56) References Cited

U.S. PATENT DOCUMENTS

| | | | | |
|---|---|---|---|---|
| 8,921,102 B2* | 12/2014 | Fuchs | ............... | B01L 3/502707 435/173.9 |
| 2012/0100538 A1* | 4/2012 | Mikolajczyk | .... | G01N 33/54306 435/6.11 |
| 2012/0202278 A1* | 8/2012 | Wagner | ................ | C12N 5/0612 435/288.7 |
| 2012/0264134 A1* | 10/2012 | Ionescu-Zanetti | ..... | C12M 41/36 435/6.13 |
| 2014/0091014 A1* | 4/2014 | Wagner | ................ | C12N 5/0612 209/579 |

\* cited by examiner

HIGH-THROUGHPUT SINGLE-CELL IMAGING, SORTING, AND ISOLATION

CROSS REFERENCE TO RELATED APPLICATIONS

This application is a continuation of and claims the benefit of U.S. patent application Ser. No. 14/595,693, filed Jan. 13, 2015, which is a continuation of and claims the benefit of U.S. patent application Ser. No. 13/783,767, filed Mar. 4, 2013, the contents of both being incorporated herein in their entirety by reference.

TECHNICAL FIELD

The present disclosure is in the field of microfluidic methods and apparatuses. In particular, described herein are methods and apparatuses for imaging, sorting, and isolating individual target cells.

BACKGROUND OF THE INVENTION

High-content analysis and isolation of cells is a growth area in personalized medicine. Both white blood cells (WBCs) and circulating tumor cells (CTCs), for example, can provide valuable information for diagnosis and treatment of diseases.

High throughput screening of WBCs can help determine whether a sick patient is responding to a specific drug or a healthy individual has mounted an adequate response to an immunization. Isolated viable WBCs can be used to determine whether specific T cell subpopulations are present in the blood and are capable of eliciting an immune response to the human immunodeficiency virus (HIV).

CTCs, i.e., tumor cells that are identified in transit within the blood stream, are shed from primary and metastatic cancers. Their isolation may be key in understanding the biology of metastasis and in a broad range of clinical applications, including early detection of cancer, the discovery of biomarkers to predict treatment responses and disease progression, as well as monitoring of minimal residual disease following and/or during treatment. Identification of CTC subsets may also allow tailoring of treatment on an individual basis.

Unfortunately, both WBCs and CTCs are rare in whole-blood samples, making their characterization and isolation problematic. Red blood cells (RBCs) typically outnumber WBCs in a whole-blood sample by a ratio of approximately 1000:1. CTCs are extraordinarily rare. An average cancer patient has approximately one to ten CTCs per milliliter of blood (one CTC for every billion blood cells).

Traditionally, gradient separations have been used to separate RBCs from various populations of WBCs. Gradient separations work on the principle that RBCs are small and dense and can form a pellet when whole blood is centrifuged. While effective, the gradient methods are typically slow, difficult to automate, and produce cells with poor viability.

Fluorescence activated cell sorting (FACS) is a well established technique for isolating CBCs from a large population of cells. However, to collect a significant sample of CTCs (e.g., about 10 CTCs) requires the screening of $10^{10}$ cells or approximately 2 mL of blood. Ideally the entire analysis should take less than an hour. Thus, the sorter must operate at a throughput of approximately 1 μL/s, corresponding to $5 \times 10^6$ cells/s. This is several orders of magnitude greater than the maximum throughput achievable using FACS. Other automated cell sorting systems are available, but these systems are typically slow, inefficient, expensive, or subject to contamination.

Because WBCs and CTCs typically comprise a very small percentage of the total number of cells in a sample and so are present in very small numbers in a sample, automated processes can be valuable in isolating these rare cells from an adequate sample. Additionally, where a sample is very small or inadequate, such as in fine needle aspirates and samples from embryos or neonates, using automated processes can be equally (if not more) valuable. Therefore, in performing cell analysis, it would be desirable in many applications to have the ability to image, sort, capture, and collect single cells in an automated and high-throughput manner that overcomes the aforementioned and other disadvantages of the prior art.

SUMMARY OF THE INVENTION

One aspect of the present invention is an apparatus for isolating individual target cells. The apparatus comprises a body structure comprising a main channel, a collection channel, and a waste channel fluidly coupled at a first fluid junction. A plurality of trapping channels intersect the collection channel, each of the trapping channels having a diameter at a location adjacent to the intersection of the trapping channel with the collection channel that is less than a diameter of an individual target cell. The apparatus further comprises an imaging system configured to image each of a plurality of individual target and non-target cells within the main channel, thereby producing imaging data; a processor configured to perform real-time, multivariate analyses of the imaging data; and a directing system configured to direct the individual target cells. A pressure source is in fluid communication with one or more of the collection channel, the waste channel, the first side channel, and the second side channel.

Another aspect of the present invention is a method for isolating individual target cells. In the method, a body structure is provided, the body structure comprising a main channel, a collection channel, and a waste channel fluidly coupled at a first fluid junction, the body structure further comprising a plurality of trapping channels intersecting the collection channel, each of the trapping channels having a trapping location adjacent to the intersection of the trapping channel with the collection channel, each of the trapping locations having a diameter that is less than a diameter of an individual target cell. A plurality of target and non-target cells are flowed through the main channel of the body structure. Imaging data are obtained for each target and non-target cell as it flows through an imaging area within the main channel. A real-time, multivariate analysis of the imaging data is performed to identify the cell corresponding to the imaging data as a target cell or a non-target cell. Where the cell is identified as a target cell, the target cell is directed into the collection channel of the body structure. A first pressure is applied to the body structure to immobilize the target cell at the trapping location of one of the plurality of trapping channels. Repeating the method steps from the obtaining imaging data step through the applying a first pressure step until all of the target cells flowing through the main channel have been immobilized or until a target cell has been immobilized at the trapping location of all of the plurality of trapping channels, whichever event occurs first. A second pressure is applied to the body structure to draw one or more of the target cells into and through the trapping channel at whose trapping location the target cell has been immobilized.

The aforementioned and other features and advantages of the invention will become further apparent from the following detailed description of the presently preferred embodiments, read in conjunction with the accompanying drawings, which are not to scale. In the drawings, like reference numbers indicate identical or functionally similar elements. The detailed description and drawings are merely illustrative of the invention, rather than limiting, the scope of the invention being defined by the appended claims and equivalents thereof.

BRIEF DESCRIPTIONS OF THE DRAWINGS

DETAILED DESCRIPTION OF THE PRESENTLY PREFERRED EMBODIMENTS

Figure 1:
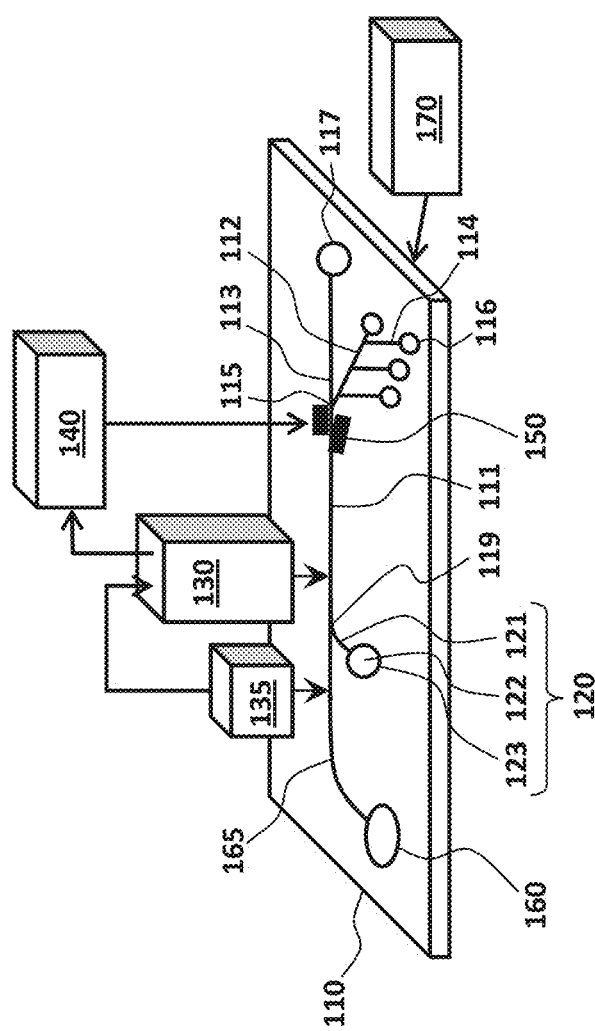
FIG. 1 is a schematic illustration of one embodiment of an apparatus for isolating individual target cells, in accordance with the present invention.

One aspect of the present invention is an apparatus for isolating individual target cells. One apparatus in accordance with the present invention is seen in FIG. 1 as comprising a body structure 110, a cell focusing system 120, an imaging system 130, a lighting and/or stimulating source 135 that operates in association with the imaging system, a processor 140, a directing system 150, a cell source 160, a sample enrichment system 165, and a pressure source 170.

Figure 2:
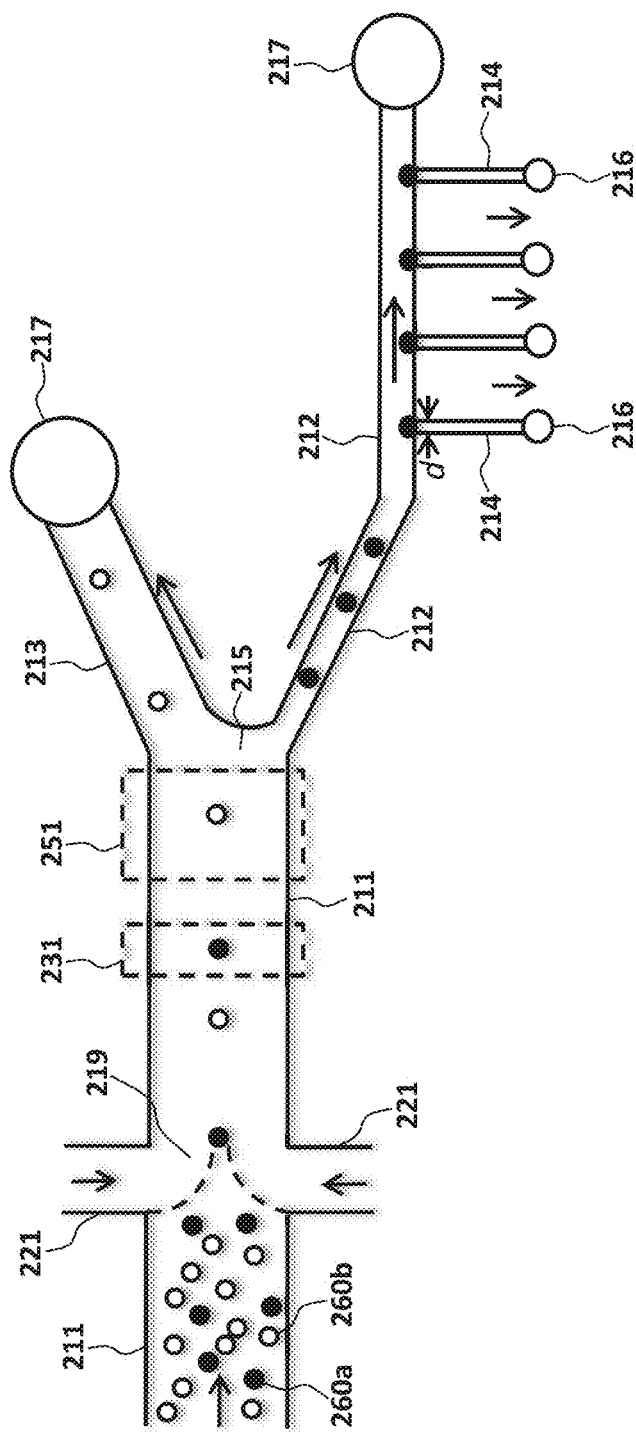
FIG. 2 is a schematic illustration of a method for isolating individual target cells, in accordance with the present invention, the figure showing components of a body structure that is an element of an apparatus for isolating individual target cells.

FIGS. 1 and 2 both illustrate body structures according to the present invention. While the outer edges of the body structure are not shown in FIG. 2, the elements illustrated in the figure are to be understood as being disposed in or on a body structure. Either or both of the illustrated body structures may be microfluidic; i.e., the body structure may be engineered to operate using small volumes of fluid (typically μl volumes of fluid) and/or may have at least one channel with a diameter ≤0.1 mm.

As seen in FIG. 1, body structure 110 comprises a main channel 111, a collection channel 112, a waste channel 113, and three trapping channels 114. Similar channels are shown in FIG. 2 at 211, 212, 213, and 214, respectively. The dimensions, arrangement, and number of channels may vary as is evident from the differences between the two exemplary body structures illustrated in the figures.

The number of trapping channels in a body structure according to the present invention may vary. For example, FIG. 1 shows three trapping channels, while FIG. 2 shows four. The figures additionally show the various channels in somewhat different configurations.

The main channel, collection channel, and waste channel are fluidly coupled at a first fluid junction. The first fluid junction may assume any functional configuration. For example, a T-shaped configuration is illustrated in FIG. 1 at 115. In this example, waste channel 113 is collinear with main channel 111, the main channel transitioning into the waste channel. Collection channel 112 is fluidly coupled to the region where main channel 111 transitions into waste channel 113. Alternatively, the main channel may be collinear with and transition into the collection channel rather than the waste channel. FIG. 2 illustrates another possible configuration in which the first fluid junction assumes a Y-shaped configuration as seen at 215.

Figure 3:
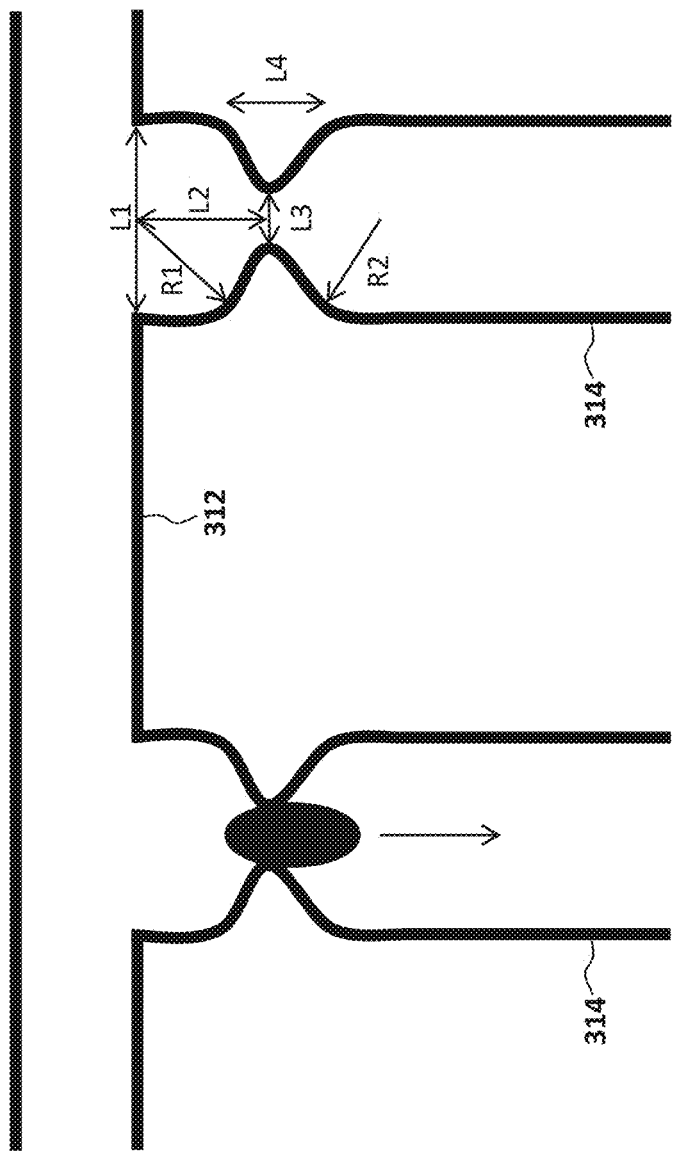
FIG. 3 is a schematic illustration of two trapping channels, in accordance with the present invention.

A plurality of trapping channels intersect the collection channel. As illustrated in FIGS. 1-3, a plurality of trapping channels 114, 214, and 314 intersect collection channels 112, 212, and 312, respectively. Each of the trapping channels has a diameter at a location adjacent to (i.e., at or near) the intersection of the trapping channel with the collection channel that is less than the diameter of an individual target cell (cell of interest) that is to be isolated by the apparatus. The diameter is indicated at d in FIG. 2 and as a variable diameter region having a length L4 in FIG. 3.

As seen in FIG. 2, the diameter of each of the trapping channels 214 is substantially the same along the length of the trapping channel, allowing a cell to be trapped at the intersection of a trapping channel 214 with collection channel 412. As seen in FIG. 3, each of the trapping channels 314 includes a region of variable diameter, with a narrowing of the diameter of the channel near the intersection of each trapping channel 314 with collection channel 312 allowing a cell to be trapped near the intersection of the trapping channel with the collection channel.

The diameter of the trapping channel (or the minimum diameter where the diameter is variable) at the location adjacent to the intersection of the trapping channel with the collection channel must be small enough to trap a target cell under a first pressure (as seen in FIG. 2), thereby blocking the entrance into the trapping channel, but still large enough to allow the cell to pass into the trapping channel (as seen in FIG. 3) under a second pressure that is greater than the first pressure. The cell may be deformed under the second pressure, thereby allowing the cell to pass through the trapping channel. Cells are typically elastic and evolutionarily engineered to withstand a wide range of flow rates and stresses in the circulatory system, and so the deformation may be temporary. Alternatively, the cell may be lysed under the second pressure, thereby allowing the contents of the cell to pass through the trapping channel.

Whether a cell is lysed or simply deformed as it passes through the trapping channel depends on a variety of factors that contribute to the pressure drop across the cell and the shear force acting on the cell. Note that cells have been shown to burst open at pressures between 25 kPa and 30 kPa (J. Kim, S. H. J. Jang, G. Jia, J. V. Zoval, N. A. Da Silva and M. J. Madou, Lab Chip, 2004, 4, 516-522).

In the embodiment seen in FIG. 3, the length (L4) of the variable radius region and the radii of curvature R1 and R2 within trapping channel 314, along with the flow rate (or applied pressure or velocity) in collection channel 312, determine the magnitude and duration of the shear force and pressure that the cell experiences as it passes through the trapping channel under the second pressure. As a first order estimate, shear force can be estimated as viscosity of fluid×velocity/L4.

Both pressure drop across the cell and shear stress on the cell surface should be considered in the design of the trapping channels to either facilitate or prevent cell lysis as the cells pass through the channels. Because the geometry of the trapping channel illustrated in FIG. 3 is complex, a detailed calculation of mechanical forces on a target cell is preferably carried out by means of computational fluid dynamics (CFD) simulations for specific target cells. Various computer programs are commercially available for this purpose.

The following design guidelines may be applied in the embodiment illustrated in FIG. 3, keeping in mind that the numerical coefficient will vary depending on the shape and morphology of the specific target cell. In these guidelines, D represents a spherical cell diameter, and L1 and L2 are as seen in FIG. 3.

$$D < L1 < 1.5D$$

$$D < L2 < 1.5D$$

$$L3 < D/2$$

Once the deformed or lysed cell has passed through the trapping channel, the cell or cell contents can be collected from a collection well disposed on a surface of the body structure and in fluid communication with the trapping channel. Such collection wells are shown at 116 in FIG. 1 and at 216 in FIG. 2. Alternatively, the trapping channel may be in fluid communication with a capillary (or other tubular member) extending from the body structure, and the cell or cell contents may be deposited into a well of a microtiter plate (e.g., a 96-well plate) or onto a glass slide via the capillary. In another alternative, the trapping channel itself may extend from the body structure, allowing a cell to be deposited into a well or onto a slide directly from the trapping channel. I.e., the trapping channels illustrated in FIG. 3 may be seen as being formed within the body structure in the same plane as collection channel 312; or collection channel 312 may be seen as being formed within the body structure, while trapping channels 314 extend from the body structure and are substantially perpendicular to a surface of the body structure.

In yet another alternative, the cell or cell contents may be flowed from the trapping channel into an analysis module that is either formed within the body structure or positioned adjacent to the body structure. For example, the trapping channel may be in fluid communication with an analysis module comprising channels and/or chambers disposed within the body structure. The collected cells or cell contents may be further analyzed using techniques such as fluorescence in situ imaging (FISH), polymerase chain reaction (PCR), cell culture, or any desired analysis method.

Non-target cells (cells not of interest) are deposited in a waste well such as is shown at 117 in FIG. 1 or are flowed to another waste location on or off the body structure.

One or more additional wells may be provided on or in the body structure as sources of the cells. One such cell reservoir is illustrated in FIG. 1 at 118. Reservoir 118 is in fluid communication with main channel 111. Alternatively, the cells may be supplied to the body structure via a flexible tube, a rigid tube, a capillary, a cannula, or another tubular member that extends out from the body structure and is in fluid communication with the main channel of the body structure.

The body structure may additionally comprise one or more focusing fluid channels. In FIG. 1, a single focusing fluid channel 121 intersects main channel 111 at a second fluid junction 119. FIG. 2 shows two focusing fluid channels 221 intersecting main channel 211 at a second fluid junction 219. Each of the focusing fluid channels is in fluid communication with a focusing fluid (e.g., a buffer), the source of which may be, for example, a focusing fluid reservoir or well such as is seen at 123 in FIG. 1 with a focusing fluid 122 disposed within the reservoir. Each of the focusing fluid channels may be in fluid communication with the same focusing fluid or different focusing fluids.

In the present embodiment, the focusing fluid channel(s), the focusing fluid, and the focusing fluid well(s) are all elements of a focusing system (indicated at 120 in FIG. 1) configured to focus a plurality of target and non-target cells into a single-file stream of cells within the main channel. Using the cell focusing system illustrated in FIG. 2, target cells 260a and non-target cells 260b are focused into a single-file stream at or near the center of main channel 211 by streams of focusing fluid simultaneously flowing into the main channel from the two focusing fluid channels 221. In the single channel alternative illustrated in FIG. 1, a single stream of focusing fluid focuses the cells into a single-file stream adjacent to the wall of the main channel that is opposite the focusing fluid channel. While hydrodynamic focusing systems have been illustrated, other focusing systems, such as acoustic or inertial focusing systems, may also be used to align the cells in a single file.

After the cells have been focused, they flow into an imaging area of the main channel such as is illustrated in FIG. 2 at 231, where they are imaged using an imaging system configured to image individual target and non-target cells in the single-file stream of cells within the main channel. Where the body structure is entirely formed using materials through which the cells can be visualized, the imaging area may be anywhere along main channel 211 downstream of the focusing system and upstream of a switching region, seen at 251 in FIG. 2. If, however, the body structure comprises opaque materials, imaging area 231 is a specific region of the body structure into which a transparent view window has been manufactured over the main channel.

The imaging system, seen at 130 in FIG. 1, may be any imaging system capable of providing one or more high-resolution and/or high-content images of each moving cell. The term "imaging" is used herein to include optical light imaging (e.g., fluorescence imaging), hyperspectral chemical imaging (e.g., Raman imaging), as well as any form of imaging by which spectra at multiple wavelengths may be collected from cells in motion. In one example, the imaging system may be an automated optical microscopy system that relies on laser-induced fluorescence. The imaging system may function in association with a lighting and/or stimulating system 135 that uses optical techniques such as laser scatter or fluorescence to improve visibility of the cells to the imaging system.

A processor, seen at 140 in FIG. 1, receives individual cell data collected using imaging system 130. Processor 140 is configured to perform real-time multivariate analyses of the collected imaging data and may be any processor capable of analyzing the imaging data to distinguish target from non-target cells based on, for example, size of the cell, which proteins are expressed on the surface of the cell, the size of the cell nucleus, whether the cell is alive or not, whether the cell is deformed, and other such relevant criteria. The processor includes instructions for identifying specific target cells; e.g., a non-transitory computer readable medium may be coupled to the processor that stores a computer program that includes information regarding the distinguishing features of the target cells. The processor is also capable of translating the results of the analysis into a signal that instructs a directing system, seen at 150 in FIG. 1, to sort out the target cells from the non-target cells.

Directing system 150 is operably connected to main channel 111 at a switching region that can be seen in FIG. 2 at 251. Within switching region 251, individual target cells 260a are directed into collection channel 212, and individual non-target cells 260b are directed into waste channel 213. The directing system is configured to direct the individual cells using one or more of a variety of methods (e.g., magnetic, dielectrophoretic, electrophoretic, hydrodynamic, laser trapping, and other methods for directing individual cells). The directing system may operate by actively directing target cells out of the single-file flow of cells into the collection channel, actively directing non-target cells out of the single-file flow of cells into the waste channel, or both.

Each apparatus includes a cell source. The cell source may be a cell reservoir or well, for example, that is disposed on a surface of the body structure as illustrated in FIG. 1 at 160. The cell source may also be external to the body structure, with the cells being introduced into the body structure through a capillary or other tubular member extending from the body structure.

When the cells of interest typically comprise a very small percentage of the total number of cells in a sample, the apparatus may also include a sample enrichment system, indicated at 165 in FIG. 1. For example, where less than 1% of the cells in the original sample are cells of interest, i.e., target cells, the concentration of these target cells within the stream of cells may be increased using methods such as aliquot-based, immunocapture-based, and size/shape/deformation-based physical enrichment methods. As illustrated in FIG. 1, the sample enrichment system employs an immunocapture-based method with target cells being captured by antibodies adsorbed to a surface of the main channel. The captured target cells are then released by, for example, a trypsin digest. Imaging of the cells begins after the cells of interest have been released, improving sensitivity and speed of analysis. Alternatively or additionally, a sample may be enriched prior to introducing the sample into the body structure.

Flow of cells through the body structure is typically pressure driven, a pressure source 170 being operably connected to the body structure. The pressure source may apply either a positive pressure at one or more upstream locations within the body structure or a negative pressure at one or more downstream locations within the body structure, or both. The pressure source is capable of applying at least a first and a second pressure, the second pressure being greater than the first.

Another aspect of the present invention is a method for isolating individual target cells. The method may be performed using an apparatus such as has been described above, taking advantage of the unique features of the apparatus.

In the method, a body structure may be provided, the body structure comprising a main channel, a collection channel, and a waste channel fluidly coupled at a fluid junction. A plurality of trapping channels intersect the collection channel, each of the trapping channels having a diameter that is less than the diameter of the target cells. Main, collection, waste, and trapping channels are indicated at 211, 212, 213, and 214, respectively, in FIG. 2, which can be seen to illustrate the present method. Arrows in FIG. 2 indicate flow directions within the channels of the body structure.

A plurality of target (260a) and non-target (260b) cells is introduced into the body structure. The cells may be, for example, deposited into a well on a surface of the body structure or introduced through a tubular member extending out from the body structure. The target and non-target cells are flowed in a stream through the main channel (211) of the body structure. Typically the cells within the channel are flowed by applying an upstream positive pressure or a downstream negative pressure; however, flow within the main channel may, alternatively, be by means of electrophoresis and/or electroosmosis.

The stream of cells is focused within the main channel such that the cells flow individually (i.e., in a single-file stream) through an imaging area located within the main channel. One such imaging area can be seen at 231 in FIG. 2. The cells may be focused using any appropriate focusing system, including, for example, hydrodynamic, acoustic, and inertial systems.

As each individual cell passes through the imaging area, imaging data for the cell are obtained using an imaging system positioned adjacent to the imaging area. The imaging data comprise one or more high-resolution and/or high-content images of the individual cell. The imaging system may be, for example, an automated optical microscopy system that is capable of providing both high-resolution and high-content imaging data for each cell. Visibility of the cells may be enhanced by a lighting and/or stimulating system that uses optical techniques such as laser scatter or fluorescence.

The imaging data for each individual cell are transmitted to a processor, where a real-time, multivariate analysis is performed on the data to identify the cell corresponding to the imaging data as a target cell or a non-target cell. The data may include, for example, information regarding the proteins expressed on the surface of the cell, the state of the nucleus of the cell, the condition of the cell, etc. Based on the analysis, each cell is identified as either a target cell (a cell of interest) or a non-target cell (a cell that is not of interest). Each cell identified as a non-target cell is directed into the waste channel (213). Each cell identified as a target cell is directed into the collection channel (212).

Once in the collection channel, each target cell is immobilized (captured or trapped) at a trapping location adjacent to (at or near) the intersection of a trapping channel with the collection channel, i.e., adjacent to the entrance into the trapping channel from the collection channel. The target cell is immobilized by a combination of the trapping channel having a diameter that is less than the diameter of the cell, thereby preventing the cell from flowing into the trapping channel, and a first pressure acting on the cell that prevents the cell from being dislodged from the trapping location by additional cells flowing past the immobilized cell. The first pressure may be either a positive pressure applied to each cell via the collection channel or a negative pressure applied to each cell via the trapping channel within whose trapping location the cell is immobilized.

The cells are trapped in sequence. I.e., the first cell identified as a target cell is trapped at the trapping location of the first of the plurality of trapping channels, the second cell identified as a target cell is trapped at the trapping location of the second of the plurality of trapping channels, and so on until the $n^{th}$ cell identified as a target cell is trapped at the trapping location of the $n^{th}$ of the plurality of trapping channels. Trapping in sequence occurs because a first target cell blocks the entrance into the first trapping channel, forcing subsequent target cells to bypass the blocked trapping channel and be immobilized at the trapping location of the next trapping channel disposed downstream in the collection channel. As a result of the cells being trapped in sequence, the cells maintain the same order within the collection channel as the order in which they were imaged, permitting the imaging data for each cell to be correlated with data obtained for the same cell in any subsequent analysis performed on the cell.

The method steps are repeated for each individual cell until either all of the target cells introduced into the body structure have been directed into the collection channel and immobilized at the trapping location of a trapping channel, or a target cell has been immobilized at the trapping location of all of the plurality of trapping channels, whichever event occurs first.

Then a second pressure that is greater than the first pressure is applied to each of the cells to draw the cell into and through the trapping channel in whose trapping location the cell has been immobilized. The cells may be drawn into and through the trapping channels individually, with each of the cells being drawn into and through its associated trapping channel individually and at a different time. Alternatively, all of the trapped cells may be drawn into their trapping channel simultaneously, or the cells may be drawn into the trapping channels in multiple groups. The second pressure can be either a positive pressure applied to each cell via the collection channel or a negative pressure applied to each cell via the trapping channel within whose trapping location the cell is immobilized.

As noted previously, each trapping channel has a diameter adjacent to the entrance that is less than the diameter of the target cell. Trapping channels may be engineered to have diameters that are only minimally smaller than the diameters of the target cells. In this alternative, the target cells, which are typically elastic, are minimally deformed during passage through the trapping channels and remain viable. Alternatively, the trapping channels may be engineered to have diameters substantially smaller than the diameters of the target cells, in which case a greater second pressure is required to draw the target cells into the trapping channels, and the cells are lysed in the process.

One skilled in the art will appreciate that where cell lysis is desired, additional methods for lysing the target cell may be applied. For example, once the desired cells have been trapped, chemical agents may be flowed into the body structure to disrupt the cell membranes. Alternatively, large electric fields may be applied to irreversibly electroporate the cells.

The cell or cell contents may be delivered into a well, such as is seen at 216 in FIG. 2, from which the cell or cell contents can be collected or within which the cell or cell contents are further analyzed. Alternatively, the cell or cell contents may be delivered into an analysis module fabricated into or associated with the body structure. For example, each trapping channel may connect with channels and/or chambers within the body structure, and further analysis may take place within these channels and/or chambers. In another example, each trapping channel may be in fluid communication with an analysis module attached or adjacent to the body structure. Further analysis of each target cell may involve FISH, PCR, cell culture, and other methods. In yet another alternative, each trapping channel may extend from the body structure and be substantially perpendicular to a surface of the body structure, allowing a cell or its contents to be deposited into a well or onto a slide directly from the trapping channel.

If the target cells typically comprise a very small percentage of the total number of cells in a sample, or if the sample is very small and, therefore, contains a limited number of cells, the concentration of these cells may be increased using methods such as aliquot-based, immunocapture-based, and size/shape/deformation-based physical enrichment methods. The enrichment may take place either before the cells are introduced into the body structure or after the cells are introduced into the body structure but before the cells are analyzed by the analysis system. Increasing the concentration of the target cells prior to the initial analysis can result in improved sensitivity and speed of analysis.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. An apparatus for isolating individual target cells, the apparatus comprising:
   a body structure comprising a main channel, a collection channel, and a waste channel fluidly coupled at a first fluid junction, the body structure further comprising a plurality of trapping channels intersecting the collection channel, each of the trapping channels having a diameter at a location adjacent to the intersection of the trapping channel with the collection channel that is less than a diameter of an individual target cell;
   an imaging system configured to image each of a plurality of individual target and non-target cells within the main channel, thereby producing imaging data;
   a processor configured to perform real-time, multivariate analyses of the imaging data;
   a directing system configured to direct the individual target cells; and
   a pressure source in fluid communication with one or more of the collection channel, and the waste channel;
   wherein the pressure source is operable to apply a pressure selected from the group consisting of a positive pressure on the collection channel, a negative pressure on the waste channel, and a combination of the positive pressure and the negative pressure, the pressure having a first pressure and a second pressure greater than the first pressure.

2. The apparatus of claim 1 wherein the diameter of the trapping channel at the location adjacent to the intersection of the trapping channel with the collection channel varies between a first diameter and a second diameter.

3. The apparatus of claim 1 further comprising a focusing system configured to focus the plurality of individual target and non-target cells into a single-file stream of cells within the main channel.

4. The apparatus of claim 1 further comprising a cell source in fluid communication with the body structure main channel.

5. The apparatus of claim 1 wherein the body structure further comprises a plurality of collection wells disposed on a surface of the body structure, each collection well in fluid communication with one of the plurality of trapping channels.

6. The apparatus of claim 1 wherein the body structure further comprises an analysis module formed within the body structure, the analysis module in fluid communication with one or more of the plurality of trapping channels.

7. The apparatus of claim 1 wherein the body structure further comprises a tubular member extending from the body structure, the tubular member in fluid communication with one or more of the plurality of trapping channels.

8. The apparatus of claim 1 wherein the trapping channels extend from the body structure and are substantially perpendicular to a surface of the body structure.

9. The apparatus of claim 1 wherein the body structure further comprises a first focusing fluid channel intersecting the main channel at a second fluid junction, and wherein the focusing system comprises a first focusing fluid in fluid communication with the first focusing fluid channel.

10. The apparatus of claim 9 wherein the body structure further comprises a second focusing fluid channel intersecting the main channel at the second fluid junction, the first and second focusing fluid channels on opposite sides of the main channel, and wherein the focusing system further comprises a second focusing fluid in fluid communication with the second focusing fluid channel.

11. The apparatus of claim 1 wherein the focusing system is one of an acoustic focusing system and an inertial focusing system.

12. The apparatus of claim 1 wherein the imaging system is an automated optical microscopy system.

13. The apparatus of claim 1 wherein a non-transitory computer readable medium is coupled to the processor, the non-transitory computer readable medium storing a computer program that includes information regarding the distinguishing features of the target cells.

14. The apparatus of claim 1 wherein the apparatus further comprises a sample enrichment system.

15. The apparatus of claim 1 wherein the apparatus further comprises one of a lighting system and a stimulating system in association with the imaging system.

16. The apparatus of claim 1 wherein the pressure source is capable of applying at least a first and a second pressure, the second pressure being greater than the first.

17. A method for isolating individual target cells, the method comprising:
- a. providing a body structure comprising a main channel, a collection channel, and a waste channel fluidly coupled at a first fluid junction, the body structure further comprising a plurality of trapping channels intersecting the collection channel, each of the trapping channels having a trapping location adjacent to the intersection of the trapping channel with the collection channel, each of the trapping locations having a diameter that is less than a diameter of an individual target cell;
- b. flowing a plurality of target and non-target cells through the main channel of the body structure;
- c. obtaining imaging data for each target and non-target cell as it flows through an imaging area within the main channel;
- d. using a processor to perform a real-time, multivariate analysis of the imaging data to identify the cell corresponding to the imaging data as a target cell or a non-target cell;
- e. where the cell is identified as a target cell, directing the target cell into the collection channel;
- f. applying a first pressure to the body structure to immobilize the target cell at the trapping location of one of the plurality of trapping channels, the first pressure being selected from the group consisting of a positive pressure on the collection channel, a negative pressure on the waste channel, and a combination of the positive pressure and the negative pressure;
- g. repeating steps c through f for each of the plurality of target and non-target cells until all of the target cells flowing through the main channel have been immobilized or until a target cell has been immobilized at the trapping location of all of the plurality of trapping channels, whichever event occurs first; and
- h. applying a second pressure to the body structure to draw one or more of the target cells into and through the trapping channel at whose trapping location the target cell has been immobilized, the second pressure being selected from the group consisting of the positive pressure on the collection channel, the negative pressure on the waste channel, and the combination of the positive pressure and the negative pressure.

18. The method of claim 17 further comprising:
focusing the plurality of target and non-target cells such that the cells flow individually through the imaging area located within the main channel before obtaining imaging data for each target and non-target cell.

19. The method of claim 17 further comprising:
where the cell is identified as a non-target cell, directing the non-target cell into the waste channel.

20. The method of claim 17 further comprising:
before obtaining imaging data for each target and non-target cell, enhancing visibility of the plurality of target and non-target cells using one of a lighting system and a stimulating system.

21. The method of claim 17 wherein the target cells are immobilized in sequence such that the first cell identified as a target cell is immobilized at the trapping location of a first of the plurality of trapping channels, the second cell identified as a target cell is immobilized at the trapping location of a second of the plurality of trapping channels, and the $n^{th}$ cell identified as a target cell is immobilized at the trapping location of an $n^{th}$ of the plurality of trapping channels.

22. The method of claim 17 wherein each target cell is drawn into and through the trapping channel at whose trapping location the cell has been immobilized individually and at a different time.

23. The method of claim 17 wherein the trapping channels extend from the body structure and are substantially perpendicular to a surface of the body structure, and wherein applying a second pressure to the body structure to draw one or more of the target cells into and through the trapping channel at whose trapping location the target cell has been immobilized comprises depositing each target cell into a well of a microtiter plate or onto a slide directly from each of the trapping channels.

* * * * *